US006335437B1

(12) United States Patent
Manoharan

(10) Patent No.: US 6,335,437 B1
(45) Date of Patent: Jan. 1, 2002

(54) METHODS FOR THE PREPARATION OF CONJUGATED OLIGOMERS

(75) Inventor: Muthiah Manoharan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/149,156

(22) Filed: Sep. 7, 1998

(51) Int. Cl.$^7$ .......................... C07H 1/00; C07H 21/00
(52) U.S. Cl. ................ 536/25.3; 536/25.31; 536/25.32; 536/23.1; 536/26.1; 536/27.1
(58) Field of Search .............................. 536/25.3, 25.31, 536/25.32, 23.1, 26.1, 27.1

(56) References Cited

U.S. PATENT DOCUMENTS

| | | | |
|---|---|---|---|
| 3,687,808 A | 8/1972 | Merigan et al. | 195/28 |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,816,571 A | 3/1989 | Andrus et al. | 536/27 |
| 4,973,679 A | 11/1990 | Caruthers et al. | 536/27 |
| 5,132,418 A | 7/1992 | Caruthers et al. | 536/27 |
| RE34,069 E | 9/1992 | Köster et al. | 536/27 |
| 5,210,264 A | 5/1993 | Yau | 558/167 |
| 5,212,295 A | 5/1993 | Cook | 536/26.7 |
| 5,371,241 A * | 12/1994 | Brush | 549/220 |
| 5,476,930 A * | 12/1995 | Letsinger et al. | 536/25.3 |

FOREIGN PATENT DOCUMENTS

EP     0 506 242 A1     3/1992

OTHER PUBLICATIONS

Alul, R.H. et al., "Oxalyl–CPG: a labile support for synthesis of sensitive oligonucleotide derivatives", *Nuc. Acid Res.*, 1991, 19, 1527–1532.

Azhayeva, E. et al., "Looped oligonucleotides form stable hybrid complexes with a single–stranded DNA", *Nucl. Acids Res.*, 1995, 23(7), 1170–1176.

Bannwarth, W., "Synthesis of Oligodeoxynucleotides by the Phosphite–Triester Method Using Dimer Units and Different Phosphorous–Protecting Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311.

Brown, T. et al., "Modern machine–aided methods of oligodeoxyribonucleotide synthesis", *Oligonucleotides and Analogs A Pratical Approach*, 1991, Chapter 1, Ekstein, F., ed., IRL Press, Oxford, 1–24.

Cook, P.D., "Medicinal chemistry of antisense oligonucleotides—future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304.

Efimov, V.A. et al., "New efficient sulfurizing reagents for the preparation of oligodeoxyribonucleotide phosphorothioate analogues", *Nucl. Acids Res.*, 1995, 23, 4029–4033.

Englisch, U. et al., "Chemically Modified Oligonucleotides as Probes and Inhibitors", *Angew. Chem. Int. Ed. Eng.*, 1991, 30, 613–629.

Goodchild, J., "Conjugates of Oligonucleotides and Modified Oligonucleotides: A Review of their synthesis and Properties", *Bioconjugate Chem.*, 1990, 1, 165–187.

Guzaev, A. et al., "A General Approach for the Hydroxy Group Functionalization of Synthetic Oligonucleotides", *Nucleotides & Nucleosides*, 1995, 14(3–5), 833–837.

Hovinen, J. et al., "Imidazole Tethered Oligodeoxyribonucleotides: Synthesis and RNA Cleaving Activity", *J. Org. Chem.*, 1995, 60, 2205–2209.

Hovinen, J. et al., "Novel Solid Supports for the Preparation of 3'–Derivatized Oligonucleotides: Introduction of 3'–Alkylphosphate Tether Groups Bearing Amino, Carboxy, Carboxamido, and Mercapto Functionalities", *Tetrahedron*, 1994, 50(24), 7203–7218.

Hovinen, J. et al., "Novel Non–Nucleoside Phosphoramidite Building Blocks for Versatile Functionalization of Oligonucleotides at Primary Hydroxy Groups", *J. Chem. Soc. Perkin Trans. I*, 1994, 2745–2749.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.* 1990, 55, 4693–4699.

Kamer, P.C.J. et al., "An Efficient Approach Toward the Synthesis of Phosphorothioate Diesters via the Schonberg Reaction", *Tetrahedron Letts.*, 1989, 30, 6757–6760.

Kroschwitz, J.I., "Polynucleotides", *Concise Encyclopedia of Polymer Science and Engineering* , 1990, John Wiley & Sons, New York, 858–859.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912.

Manoharan, M. et al., "Oligonucleotides Bearing Cationic Groups: $N^2$–(3–Aminopropyl)deoxyguanosine. Synthesis, Enhanced Binding Properties and Conjugation Chemistry", *Tetra. Lett.*, 1996, 37(43), 7675–7678.

(List continued on next page.)

Primary Examiner—James O. Wilson
Assistant Examiner—Howard Owens
(74) *Attorney, Agent, or Firm*—Woodcock Washburn Kurtz Mackiewicz & Norris LLP

(57) ABSTRACT

The present invention provides novel methods for preparing oligonucleotide conjugates using a novel electrophilic haloacetyl linker. Novel compounds and intermediates are also disclosed.

41 Claims, No Drawings-

OTHER PUBLICATIONS

Manoharan, M. et al., "2'–O–and 3'–O–Pyrimidine Aminothether–Containing Oligonucleotides: Synthesis and Conjugation Chemistry", *Tetrahedron Letts.*, 1995, 36, 3647–3650.

Miura, K. et al., "Blockwise Mechanical Synthesis of Oligonucleotides by the Phosphoramidite Method", *Chem Pharm. Bull.*, 1987, 35, 833–836.

Ouchi, T. et al., "Synthesis and Antitumor Activity of Poly(Ethylene Glycol)s Linked to 5–40 –Fluorouracil via a Urethane or Urea Bond", *Drug Des. & Disc.*, 1992, 9, 93–105.

Rao, M.V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Secrist, J.A. et al., "Synthesis and Biological Activity of 4–40–Thionucleosides", *10th International Rountable: Nucleosides, Nucleotides and their Biological Applications*, Sep. 16–20 1992, Abstact 21, Park City, Utah, 40.

Stec, W.J. et al., "Bis (O,O–Diispropoxy Phosphinothioyl) Disulfide—A Highly Efficient Sulfurizing Reagent for Cost–Effective Synthesis of Oligo(Nucleoside Phosphorothioate)s", *Tetrahedron Letts.*, 1993, 34, 5317–5320.

Stec, W.J. et al., "Stereospecific Synthesis of P–chiral Analogs of oligonucleotides", *Methods in Molecular Biology*, 20, 1993, Chapter 14, Humana Press, Totowa, NJ, 285–313.

Stec, W.J. et al., "Novel route to oligo(deoxyribonucleoside phosphorothioates). Stereocontrolled synthesis of P–chiral oligo(deoxyribonucleoside phosphorothioates)", *Nucl. Acids Res.*, 1991, 19, 5883–5888.

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32(26), 3005–3008.

Wolter, A. et al., Polymer Support Oligonucleotide Synthesis XX: Synthesis of a Henhectacosa Deoxynucleotide by use of a Dimeric Phosphoramidite *Nucleosides & Nucleotides*, 1986, 5, 65–77.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

Wu, H. et al., "Inhibition of in vitro transcription by specific double–stranded oligodeoxyribonucleotides", *Gene*, 1990, 89, 203–209.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.*, 1996, 24, 1602–1607.

Xu, Q. et al., "Efficient introduction of phosphorothioates into RNA oligonucleotides by 3–ethoxy–1,2, 4–dithiazoline–5–one (EDITH)", *Nucl. Acids Res.*, 1996, 24, 3643–3644.

* cited by examiner

METHODS FOR THE PREPARATION OF CONJUGATED OLIGOMERS

FIELD OF THE INVENTION

This invention relates to methods for the preparation of oligomeric compounds having pendant groups conjugated thereto through a novel haloacetyl linker. This invention also relates to compounds containing such haloacetyl linkers, and to methods and intermediates useful for their preparation.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

Synthetic oligonucleotides having 5'-terminal functional or reporter groups are employed in a number of bioanalytical and antisense applications. Appropriately, a number of procedures and reagents that allow their preparation have been described, including conjugation of electrophiles to oligonucleotides via tethers carrying nucleophilic groups. For the opposite process of conjugating nucleophiles to electrophilic sites, the methods available to generate these sites in oligonucleotides are limited. These include periodate oxidation of a terminal ribose moiety or the use of an internal abasic site within the oligonucleotide sequence. Heterobifunctional reagents that bear a phosphoramidite moiety along with an electrophilic functional group that is reactive in orthogonal conditions are therefore of particular interest.

One group have reported methods that utilize the reactivity of (thio)ester group towards alkylamines. See Hovinen, J., Guzaev, A., Azhayeva, E., Azhayev, A. and Lönnberg, H. *J. Org. Chem.* 1995, 60, 2205; Azhayeva, E., Azhayev, A., Guzaev, A., Hovinen, J. and Lönnberg, H. *Nucleic Acids Res.* 1995, 23, 1170; Guzaev, A., Hovinen, J., Azhayev, A. and Lönnberg, H. *Nucleoides & Nucleotides* 1995, 14, 833; Hovinen, J., Guzaev, A., Azhayev, A. and Lönnberg, H. *J. Chem. Soc. Perkin Trans. I* 1994, 2745; and Hovinen, J., Guzaev, A., Azhayev, A., and Lönnberg, H. *Tetrahedron,* 1994, 50, 7207. On completion of chain elongation, the modified oligonucleotide could be converted into a variety of conjugates by treatment with linkers of different length and substituents that bear a primary amino group.

A haloacetyl linker that is reactive towards a variety of nucleophiles has been introduced previously into oligonucleotides by postsynthetic reaction in solution. See Goodchild, *J. Bioconjugate Chem.* 1990, 1, 165. Ligands carrying amino groups may be either less available or less desirable for attachment than those with other nucleophilic groups. Therefore, more universal methods for preparation of oligonucleotide conjugates with the aid of heterobifunctional phosphoramidite building blocks are greatly desirable. This invention is directed to this, as well as other, important ends.

SUMMARY OF THE INVENTION

In accordance with one aspect of the present invention, methods are provided for the preparation of a conjugated oligonucleotide comprising:

providing a compound of Formula I:

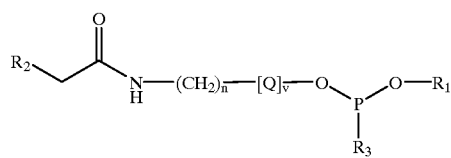

wherein:

$R_1$ is a phosphorus protecting group;

$R_2$ is chlorine or a pendant group;

$R_3$ is —N($R_4$)$_2$, or a heterocycloalkyl or heterocycloalkenyl ring containing from 4 to 7 atoms, and having up to 3 heteroatoms selected from nitrogen, sulfur, and oxygen;

$R_4$ is straight or branched chain alkyl having from 1 to 10 carbons.

v is 0 or 1;

n is 1 to about 10;

Q has one of the Formulas II or III:

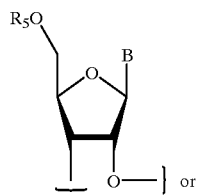

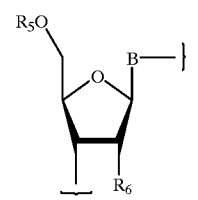

wherein:

$R_5$ is a hydroxyl protecting group;

B is a nucleobase;

$R_6$ is F, O—$R_{20}$, S—$R_{20}$ or N—$R_{20}$($R_{21}$)

$R_{20}$ is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;

and wherein any available hydrogen atom of said ring system is each replaceable with an alkoxy, alkylamino, urea or alkylurea group;

or $R_2$, has one of the formulas:

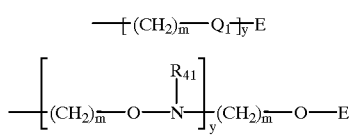

wherein $Q_1$ is O, S or $NR_2$;

m is from 1 to 10;

y is from 0 to 10;

E is N($R_{21}$) ($R_{31}$), N=C($R_{21}$) ($R_{31}$), $C_1$–$C_{10}$ alkyl, or $C_1$–$C_{10}$ substituted alkyl wherein said substituent is N ($R_2$) ($R_3$);

each $R_{21}$ and $R_{31}$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and $R_{41}$ is H or $C_1$–$C_{12}$ alkyl;

reacting said compound of Formula I with a compound of Formula IV:

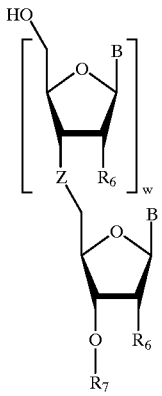

IV wherein:

$R_7$ is H, a hydroxyl protecting group, or a linker connected to a solid support;

w is 0 to about 100;

to form a compound of Formula IVa:

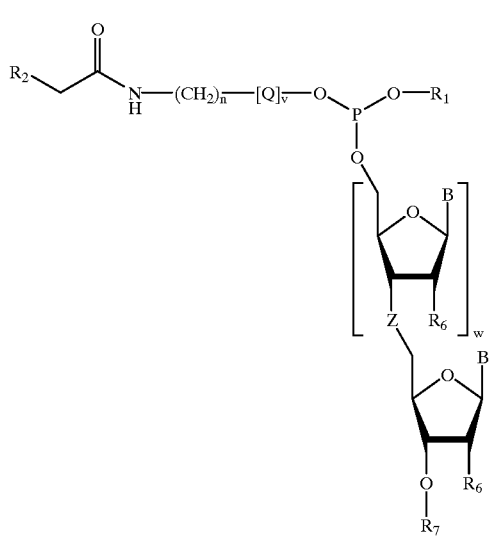

IVa and contacting the compound of Formula IVa with a pendant group for a time and under conditions sufficient to form said conjugate.

Some preferred embodiments of the methods of the invention further comprise oxidizing or sulfurizing the compound of Formula IVa to form a compound of Formula IVb:

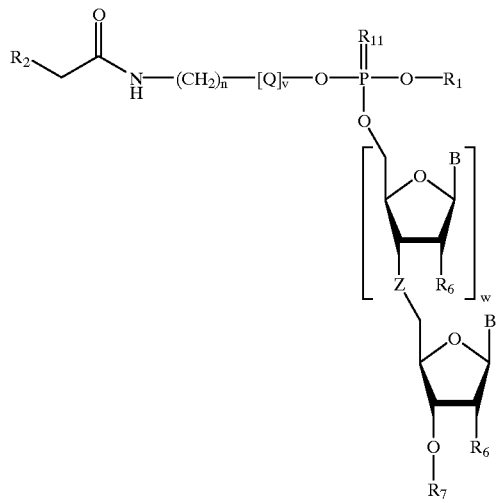

wherein $R_{11}$ is O or S.

In some preferred embodiments, v is 0. In further preferred embodiments, v is 1. In still further preferred embodiments, $R_2$ is Cl. In yet further preferred embodiments, $R_2$ is Cl and $R_3$ is $-N(R_4)_2$, wherein $R_4$ is isopropyl.

In further preferred embodiments, $R_2$ is Cl, $R_3$ is $-N(R_4)_2$, wherein $R_4$ is isopropyl, and $R_1$ is β-cyanoethyl, $-CH_2CH=CHCH_2CN$, para-$CH_2C_6H_4CH_2CN$, $-(CH_2)_{2-5}N(H)COCF_3$, $-CH_2CH_2Si(C_6H_5)_2CH_3$, or $CH_2CH_2N(CH_3)COCF_3$, with β-cyanoethyl being preferred.

In some preferred embodiments, n is 2 to 8, with 4 to 6 being preferred, and 6 being more preferred.

In some preferred embodiments of the methods of the invention, $R_7$ is a linker connected to a solid support.

In some preferred embodiments, the pendant group is an amine, a polyamine, a thiol, a protein, a peptide, or an amino acid.

In some preferred embodiments, v is 0, $R_2$ is Cl, $R_3$ is $-N(R_4)_2$, wherein $R_4$ is isopropyl, $R_1$ is β-cyanoethyl, n is 6, $R_7$ is a linker connected to a solid support, and said pendant group is an amine, a polyamine, a thiol, a protein, a peptide, or an amino acid.

In other preferred embodiments, v is 1, $R_2$ is Cl, $R_3$ is $-N(R_4)_2$, wherein $R_4$ is isopropyl, $R_1$ is β-cyanoethyl, n is 6, $R_7$ is a linker connected to a solid support, and said pendant group is an amine, a polyamine, a thiol, a protein, a peptide, or an amino acid, and Q has the Formula II.

In still further preferred embodiments, V is 1, $R_2$ is Cl, $R_3$ is $-N(R_4)_2$, wherein $R_4$ is isopropyl, $R_1$ is β-cyanoethyl, n is 6, $R_7$ is a linker connected to a solid support, and said pendant group is an amine, a polyamine, a thiol, a protein, a peptide, or an amino acid, and Q has the Formula III.

Also provided in accordnce with the present invention are synthetic methods comprising:

providing a compound of Formula $H_2N-(CH_2)_n-OH$ wherein n is 1 to about 10;

reacting said compound with a compound of Formula VIII:

VIII

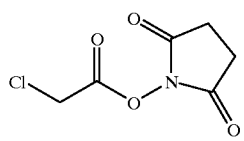

to form a chloroacetylamino alkanol compound of Formula IX:

IX

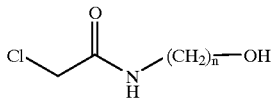

and contacting said chloroacetylamino alkanol compound with a reagent of Formula $(R_3)_2P$—O—$R_1$
wherein:

$R_1$ is a phosphorus protecting group;

$R_3$ is —$N(R_4)_2$, or a heterocycloalkyl or heterocycloalkenyl ring containing from 4 to 7 atoms, and having up to 3 heteroatoms selected from nitrogen, sulfur, and oxygen;

$R_4$ is straight or branched chain alkyl having from 1 to 10 carbons.

n is 1 to about 10;

for a time and under conditions sufficient to form an activated phosphate compound of Formula X:

X

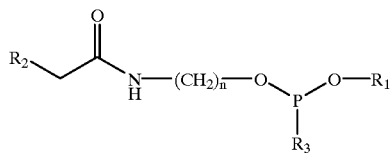

In some preferred embodiments, $R_3$ is diisopropylamino; and $R_1$ is β-cyanoethyl.

Further preferred embodiments of the methods of the inventikon further comprise reacting said activated phosphate compound with a free hydroxyl group of a nucleoside, a nucleotide, an oligonucleotide, or an oligonucleotide connected to a solid support to form a compound of Formula XI:

XI

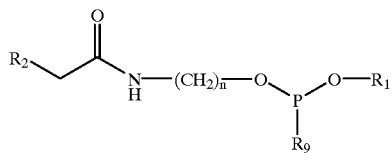

wherein $R_9$ is a nucleoside, a nucleotide, an oligonucleotide, or an oligonucleotide connected to a solid support.

Still further preferred embodiments further comprise oxidizing or sulfurizing said compound of Formula XI to form a compound of Formula XII:

XII

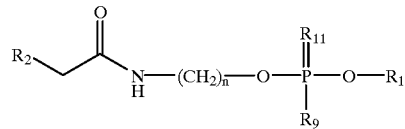

wherein $R_{11}$ is O or S.

Still further preferred embodiments further comprise coupling a pendant group to the compound of Formula XII, preferably wherein said pendant group is an amine, a polyamine, a thiol, a protein, a peptide, or an amino acid.

The invention also provides novel compounds having the Formula V:

V

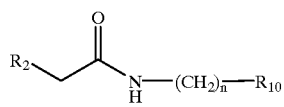

wherein:

$R_2$ is halogen or a pendant group;

$R_{10}$ is a nucleobase, a nucleoside, a nucleotide, an activated nucleotide, an oligonucleotide, an oligonucleotide connected to a solid support, or a moiety of Formula VI:

VI $$-O\underset{R_3}{\overset{}{P}}O-R_1$$

wherein:

$R_1$ is H or a phosphorus protecting group;

$R_3$ is —$N(R_4)_2$, or a heterocycloalkyl or heterocycloalkenyl ring containing from 4 to 7 atoms, and having up to 3 heteroatoms selected from nitrogen, sulfur, and oxygen;

$R_4$ is straight or branched chain alkyl having from 1 to 10 carbons; and n is from 1 to about 10.

In some preferred embodiments, $R_{10}$ is a nucleoside, a nucleotide, an activated nucleotide, an oligonucleotide, or an oligonucleotide connected to a solid support. In further preferred embodiments $R_{10}$ has the Formula IV.

In some preferred embodiments, compounds of the invention have the Formula VII:

VII

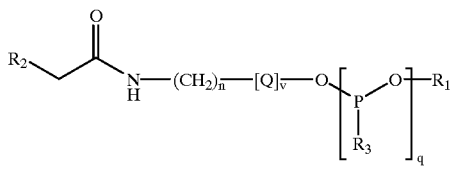

wherein:

v is 0 or 1;

q is 0 or 1;

Q has one of the Formulas II or III:

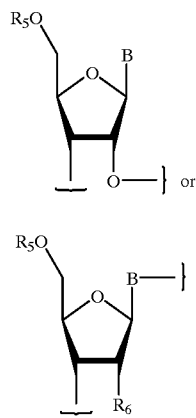

wherein:
$R_5$ is a hydroxyl protecting group;
B is a nucleobase;
$R_6$ is F, O—$R_{20}$, S—$R_{20}$ or N—$R_{20}$ ($R_{21}$)
$R_{20}$ is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;
and wherein any available hydrogen atom of said ring system is each replaceable with an alkoxy, alkylamino, urea or alkylurea group;
or $R_{20}$ has one of the formulas:

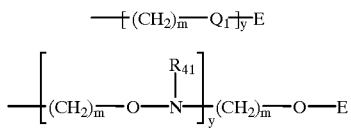

wherein
$Q_1$ is O, S or $NR_2$;
m is from 1 to 10;
y is from 0 to 10;
E is $N(R_{21})(R_{31})$, $N=C(R_{21})(R_{31})$, $C_1$–$C_{10}$ alkyl, or $C_1$–$C_{10}$ substituted alkyl wherein said substituent is $N(R_2)(R_3)$;
each $R_{21}$ and $R_{31}$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and
$R_{41}$ is H or $C_1$–$C_{12}$ alkyl.

In some preferred embodiments, v is 0 and q is 1. In further preferred embodiments, v is 1. In further preferred embodiments, v is 1 and q is 1.

In some preferred embodiments, $R_2$ is Cl. In further preferred embodiments, $R_2$ is Cl and $R_3$ is —$N(R_4)_{21}$ wherein $R_4$ is isopropyl. In still further preferred embodiments, $R_2$ is Cl, $R_3$ is —$N(R_4)_2$, wherein $R_4$ is isopropyl, and $R_1$ is β-cyanoethyl, —$CH_2CH=CHCH_2CN$, para-$CH_2C_6H_4CH_2CN$, —$(CH_2)_{2-5}N(H)COCF_3$, —$CH_2CH_2Si(C_6H_5)_2CH_3$, or $CH_2CH_2N(CH_3)COCF_3$, with β-cyanoethyl being preferred.

Preferably, n is 2 to 8, with 4 to 6 being more preferred, and 6 being especially preferred.

In some preferred embodiments, v and q are each 1; and Q has the Formula III wherein the moiety —O—P($R_3$)—O—$R_1$ is attached to B at the $N^2$ position.

In further preferred embodiments, v and q are each 1; and Q has the Formula II wherein the moiety —O—P($R_3$)—O—$R_1$ is attached at the 2'-position.

In some preferred embodiments, said pendant group is an amine, a polyamine, a thiol, a protein, a peptide, or an amino acid.

In some especially preferred embodiments, v is 0; q is 1; $R_2$ is Cl, $R_3$ is —$N(R_4)_2$, wherein $R_4$ is isopropyl, $R_1$ is β-cyanoethyl, n is 6, and said pendant group is an amine, a polyamine, a thiol, a protein, a peptide, or an amino acid.

In further especially prefered embodiments, v and q are each 1; $R_2$ is Cl, $R_3$ is —$N(R_4)_2$, wherein $R_4$ is isopropyl, $R_1$ is β-cyanoethyl, n is 6, said pendant group is an amine, a polyamine, a thiol, a protein, a peptide, or an amino acid, and Q has the Formula II wherein the moiety —Q—P($R_3$)—O—$R_1$ is attached at the 2'-position.

In yet further especially preferred embodiments $R_2$ is Cl, $R_3$ is —$N(R_4)_2$, wherein $R_4$ is isopropyl, $R_1$ is β-cyanoethyl, n is 6, said pendant group is an amine, a polyamine, a thiol, a protein, a peptide, or an amino acid, and Q has the Formula III wherein the moiety —O—P($R_3$)—O—$R_1$ is attached at the $N^2$-position.

DESCRIPTION OF PREFERRED EMBODIMENTS

In one aspect, the present invention provides methods for the preparation of oligomeric compounds having at least one pendant group conjugated thereto. In accordance with the methods of the invention, conjugation of the pendant group to the oligomeric compound is achieved by use of a novel electrophilic haloacetyl linker of formula $R_2$—$CH_2$—C(=O)—NH—$(CH_2)_n$— wherein n is from 1 to about 10 and $R_2$ is halogen, which is preferably chlorine.

In accordance with some preferred embodiments of the methods of the invention, a compound of Formula I:

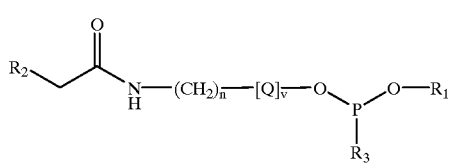

wherein the constituent variables are as previously defined, is reacted with the 5'-hydroxyl of a nucleoside, nucleotide, oligonucleotide, or oligonucleotide connected to a solid support as represented by Formula IV:

IV

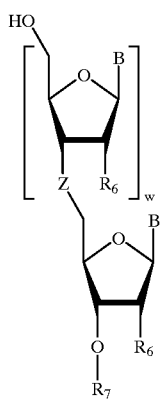

to produce a phosphite compound of Formula IVa:

IVa

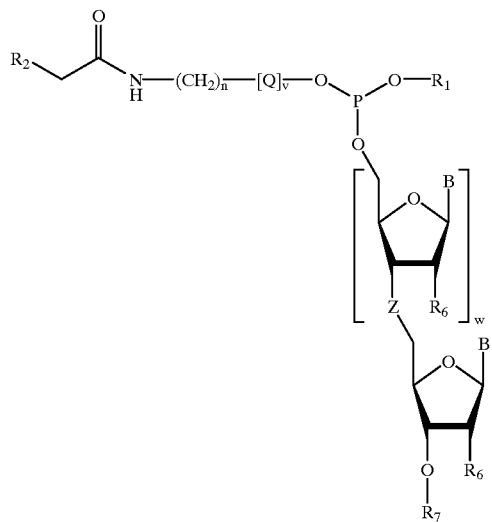

In some preferred embodiments, the phosphite linkage is then oxidized or sulfurized by standard techniques to form a phosphotriester or phosphorothiotriester linkage, as represented by Formula IVb:

IVb

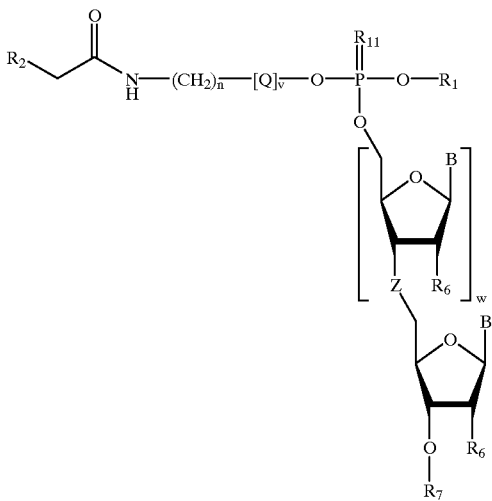

wherein $R_{11}$ is O or S.

The compound of Formula IVb is then contacted with a pendant group having, in preferred embodiments, a primary amino or thio group, for a time and under conditions sufficient to form the conjugate.

As used herein, the term "reacting" means placing the indicated moieties together under conditions that will cause the moieties to perform the chemical reaction indicated.

As used herein, the term contacting means placing the indicated moieties together in a container under conditions that will cause the indicated reaction to occur.

As used herein, the term "pendant group" means a functional or reporting group as is used in bioanalytical and/or antisense applications. Representative pendant groups include amines such as long and short straight, branched chain or cyclic alkylamines, polyamines such as spermine and spemidiine, polyalkylamines, thiols including aliphatic and aromatic mercaptans such as n-$C_{18}H_{37}SH$, thiocresol, benzylmercaptan, and thiocholesterol, proteins, peptides, and amino acids.

A wide variety of such pendant groups are amenable to the present invention. It is only required that the pendant group have a nucleophilic moiety such as an amino group, a sulfur atom, or an oxygen atom which is capable of displacing the halogen atom of the electrophilic linker and thus effecting the linkage of to the pendant group.

In some preferred embodiments, the haloacetyl linker is incorporated into an activated nucleoside phosphoramidite synthon (i.e., embodiments wherein variable "v" is 1 in the Formulas herein).

The electrophilic haloacetyl linker can be attached to an activated nucleoside phosphoramidite synthon at the sugar moiety thereof, preferably through the 2'-hydroxyl (e.g., embodiments wherein variable "v" is 1 and Q has Formula II). The electrophilic haloacetyl linker also can be attached to an activated nucleoside phosphoramidite synthon at the base moiety thereof, preferably through the N-2 nitrogen (e.g., embodiments wherein variable "v" is 1 and Q has Formula III).

The electrophilic haloacetyl linker also can be attached to the intersugar linkage of an oligonucleotide. Acordingly, in some preferred embodiments, the linker can be prepared as a phosphoramidite (e.g., embodiments wherein variable "v" is 0 in the Formulas herein) of Formula X:

X

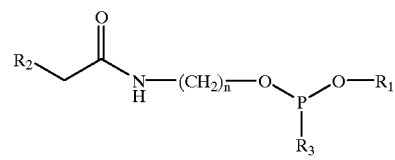

wherein the constituent variables are as described supra. Such compounds can be advantageously employed to attach the haloacetyl linker to, for example, the 5'-terminal hydroxyl of a completed oligonucleotide chain using standard phosphoramdite oligonucleotide synthetic regimes. Thus, in accordance with the methods of the invention, the haloacetyl linker can be conveniently introduced into an oligonucleotide during standard oligonucleotide synthesis at the 3'-terminus, the 5'-terminus, or at any position in the oligonucleotide.

The methods of the invention provide the additional feature that a pendant group of interest can be attached postsynthetically to the fully protected support-bound oligonucleotide via either thiol or primary amino group. In an additional advantage provided by the methods of the invention, the postsynthetic coupling of pendant group may be carried our both in aqueous and organic solvent.

In preferred embodiments, the concentration of the compound to be attached is from about 0.05M to about 1.0M.

It is preferred that the coupling of pendant groups through thiol groups be performed in the presence of a tertiary amine as a catalyst, preferably from about 0.5M to about 1.0M. Suitable preferred catalysts include triethylamine, ethyldiisopropylamine, and 1,8-diazabicyclo[4.5.0]undec-7-ene (DBU).

At the completion of the last coupling of the oligonucleotide synthetic cycle, the resulting oligonucleotide having the electrophilic haloacetyl linker attached thereto is typically coupled to a pendant group through the linker, and the completed oligomer is then released from the solid support and simultaneously deprotected by contacting with aqueous ammonia. Typical isolated yields of modified oligonucleotides is 20 to 70% depending on the length of the oligonucleotide, and the reactivity of particular pendant group.

The methods of the invention can be used to prepare oligomers having a variety of internucleoside linkages, represented by Z in the formulas herein. These include phosphodiester, phosphotriester, and phosphorothioate linkages.

The oligonucleotides prepared by the methods of the invention can have a wide variety of substitutents at their 2'-positions, in addition to the haloacetyl linker described herein. These include those described for substituent $R_6$ of the formulas described herein.

The methods of the invention provide for oligonucleotides having one, two or a plurality of pendant groups attached through novel linkers described herein.

In some preferred embodiments, compounds of Formula X:

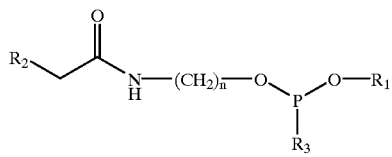

are prepared by providing a compound of Formula $H_2N$—$(CH_2)_n$—OH wherein n is 1 to about 10;

reacting the compound with a compound of Formula VIII:

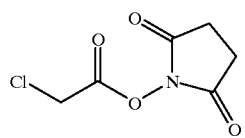

to form a chloroacetylamino alkanol compound of Formula IX:

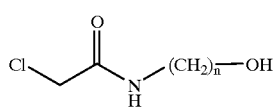

and contacting said chloroacetylamino alkanol compound with a reagent of Formula $(R_3)_2P$—O—$R_1$ for a time and under conditions sufficient to form the activated phosphate compound of Formula X:

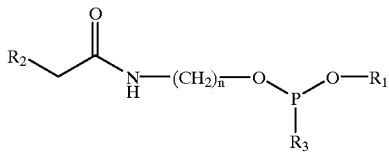

In preferred embodiments, the reaction of the compound of Formula $H_2N$—$(CH_2)_n$—OH with the compound of Formula VIII, and the contacting of the chloroacetylamino alkanol compound of Formula IX with the reagent of Formula $(R_3)_2P$—O—$R_1$ is preferably performed in an organic solvent, the selection of which is within the skil of htose in the art.

The methods of the present invention can further include reacting the activated phosphate compound of formula X with a free hydroxyl group of a nucleoside, a nucleotide, an oligonucleotide, or an oligonucleotide connected to a solid support to form a compound of Formula XI:

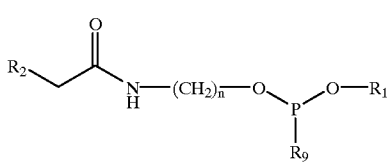

wherein $R_9$ is a nucleoside, a nucleotide, an oligonucleotide, or an oligonucleotide connected to a solid support. Preferably, this is carried out in according to standard solid phase phosphoramidite synthetic protocols.

The phosphite compound of Formula XI is then preferably oxidizing or sulfurized to form a compound of Formula XII:

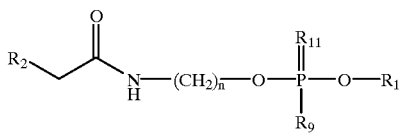

wherein $R_{11}$ is O or S, according to methodologies disclsoed supra. A pendant group is then coupled to the compound of Formula XII, as described supra.

The methods of the present invention are useful for the preparation of oligomeric compounds containing monomeric subunits that are joined by a variety of linkages, including phosphite, phosphodiester, phosphorothioate, and/or phosphorodithioate linkages. As used herein, the term "oligomeric compound" is used to refer to compounds containing a plurality of nucleoside monomer subunits that are joined by internucleoside linkages, preferably phosphorus-containing linkages, such as phosphite, phosphodiester, phosphorothioate, and/or phosphorodithioate linkages. The terms "oligomeric compound" or "oligomer" therefore includes naturally occurring oligonucleotides, their analogs, and synthetic oligonucleotides. Monomer or higher order synthons having the Formulas described herein include both native (i.e., naturally occurring) and synthetic (e.g., modified native or totally synthetic) nucleosides and nucleotides.

Methods for coupling compounds of Formula I and Formula IV of the invention include both solution phase and, preferably, solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. See for example, *Oligonucleotides And Analogues A Practical Approach,* Ekstein, F. Ed., IRL Press, N.Y, 1991, hereby incorporated by reference in its entirety. The support-bound monomer or higher order first synthon is then treated to remove the 5'-protecting group, typically by treatment with acid. The solid support bound monomer is then reacted with a nucleoside phosphoramidite under anhydrous conditions in the presence of an activating agent such as, for example, 1H-tetrazole, 5-(4-nitrophenyl)-1H-tetrazole, or diisopropylamino tetrazolide to form a phosphite triester linkage.

The phosphite triester linkage is subsequently oxidized or sulfurized. Choice of oxidizing or sulfurizing agent will determine whether the linkage will be oxidized or sulfurized to a phosphotriester, thiophosphotriester, or a dithiophosphotriester linkage.

It is generally preferable to perform a capping step, either prior to or after oxidation or sulfurization of the phosphite triester, thiophosphite triester, or dithiophosphite triester. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

Treatment with an acid removes the 5'-hydroxyl protecting group, and the synthetic cycle is repeated until the desired oligomer is achieved. At any point in the iterative cycle, a compound of the invention having, for example, Formula I, can be introduced into the oligonucleotide chain. Thus, the methods of the invention provide for the introduction of linked pendant groups at any position in the oligomeric chain.

After the coupling of the final phosphoramidite synthon, the completed oligomer is then cleaved from the solid support. The cleavage step, which can precede or follow deprotection of protected functional groups, will in preferred embodiments yield the completed oligomer free from the solid support, and devoid of all phosphorus protecting groups; that is, during cleavage, the linkages between monomeric subunits are converted from phosphotriester, thiophosphotriester, or dithiophosphotriester linkages to phosphodiester, phosphorothioate, or phosphorodithioate linkages.

The internucleoside linkages of the oligomeric compounds described herein, represented by moiety Z in the compounds and methods described herein, can be any internucleoside linkage as is known in the art, including phosphorus based linking groups such as phosphite, phosphodiester, phosphorothioate, and phosphorodithioate linkages. Such linkages can be protected, i.e., they can bear, for example, phosphorus protecting groups. As used herein, the term "phosphorus protecting group" is intended to denote protecting groups that are known to be useful to protect phosphorus-containing linkages during oligonucleotide synthesis. One such preferred phosphorus protecting group is the β-cyanoethyl protecting group.

Other representative phosphorus protecting groups include —$CH_2CH$=$CHCH_2CN$, para-$CH_2C_6H_4CH_2CN$, —$(CH_2)_{2-5}N(H)COCF_3$, —$CH_2CH_2Si(C_6H_5)_2CH_3$, —$CH_2CH_2N(CH_3)COCF_3$ and others known in the art.

In preferred embodiments, the methods of the invention are used for the preparation of oligomeric compounds, preferably oligonucleotides. As used herein, the term "oligonuclotide" means compounds that can contain both naturally occurring (i.e. "natural") and non-naturally occurring ("synthetic") moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

Representative nucleobases useful in the compounds and methods described herein include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application,* Ed. S. T. Crooke and B. Lebleu, CRC Press, 1993, in Englisch et al., *Angewandte Chemie,* International Edition, 1991, 30, 613–722 (see especially pages 622 and 623, and in the *Concise Encyclopedia of Polymer Science and Engineering,* J. I. Kroschwitz Ed., John Wiley & Sons, 1990, pages 858–859, Cook, P. D., *Anti-Cancer Drug Design,* 1991, 6, 585–607, each of which are hereby incorporated by reference in their entirety. The term 'nucleosidic base' is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

Representative 2' sugar modifications (position $R_1$) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Sugars having O-substitutions on the ribosyl ring are also amenable to the present invention. Representative substitutions for ring 0 include S, $CH_2$, CHF, and $CF_2$, see, e.g., Secrist, et al., Abstract 21, *Program & Abstracts, Tenth International Roundtable, Nucleosides, Nucleotides and their Biological Applications,* Park City, Utah, Sep. 16–20, 1992, hereby incorporated by reference in its entirety.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. As used herein, the term "lower alkyl" is intended to mean alkyl having 6 or fewer carbons.

As used herein, the term "aralkyl" denotes alkyl groups which bear aryl groups, for example, benzyl groups. The term "alkaryl" denotes aryl groups which bear alkyl groups, for example, methylphenyl groups. As used herein the term "aryl" denotes aromatic cyclic groups including but not limited to phenyl, naphthyl, anthracyl, phenanthryl, and pyrenyl.

As used herein, the term "alkanoyl" has its accustomed meaning as a group of formula —C(=O)-alkyl. A preferred alkanoyl group is the acetyl group.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention $R_7$ can be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach,* Ekstein, F. Ed., IRL Press, N.Y, 1991, Chapter 1, pages 1–23.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., *Tetrahedron Letters* 1993, 34, 3373, hereby incorporated by reference in its entirety) and Poros—a copolymer of polystyrene/divinylbenzene.

In some preferred embodiments of the invention $R_7$ or $R_5$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis,* Chapter 2, 2d ed, John Wiley & Sons, New York, 1991, each of which are hereby incorporated by reference in their entirety. Preferred protecting groups used for $R_7$ or $R_5$ include dimethoxytrityl (DMT), monomethoxytrityl, 9-phenylxanthen-9-yl (Pixyl) and 9-(p-methoxyphenyl)xanthen-9-yl (Mox). The $R_7$ or $R_5$ group can be removed from oligomeric compounds of the invention by techniques well known in the art to form the free hydroxyl.

For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or to other groups such as, for example, to 2'-alkoxy groups. Such amino groups are also commonly present in naturally occurring and non-naturally occurring nucleobases. It is generally preferred that these amino groups be in protected form during the synthesis of oligomeric compounds of the invention. epresentative amino protecting groups suitable for these purposes are discussed in Greene and Wuts, *Protective Groups in Organic Synthesis,* Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, R. P., et. al., *J. Chem. Soc.,* 1990, 112, 1253–1254, and Iyer, R. P., et. al., *J. Org. Chem.,* 1990, 55, 4693–4699); tetraethylthiuram disulfide (see e.g., Vu, H., Hirschbein, B. L., *Tetrahedron Lett.,* 1991, 32, 3005–3008); dibenzoyl tetrasulfide (see e.g., Rao, M. V., et. al., *Tetrahedron Lett.,* 1992, 33, 4839–4842); di(phenylacetyl)disulfide (see e.g., Kamer, P. C. J., *Tetrahedron Lett.,* 1989, 30, 6757–6760); Bis(O,O-diisopropoxy phosphinothioyl)disulfids (see Stec et al., *Tetrahedron Lett.,* 1993, 34, 5317–5320); 3-ethoxy-1,2,4-dithiazoline-5-one (see *Nucleic Acids Research,* 1996 24, 1602–1607, and

*Nucleic Acids Research,* 1996 24, 3643–3644); Bis(p-chlorobenzenesulfonyl)disulfide (see *Nucleic Acids Research,* 1995 23, 4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention are preferably hybridizable to a specific target preferably comprise from about 5 to about 50 monomer subunits. It is more preferred that such compounds comprise from about 10 to about 30 monomer subunits, with 15 to 25 monomer subunits being particularly preferrred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, K., et al., *Chem. Pharm. Bull.,* 1987, 35, 833–836; Kumar, G., and Poonian, M. S., *J. Org. Chem.,* 1984, 49, 4905–4912; Bannwarth, W., *Helvetica Chimica Acta,* 1985, 68, 1907–1913; Wolter, A., et al., *nucleosides and nucleotides,* 1986, 5, 65–77, each of which are hereby incorporated by reference in their entirety.

In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

Compounds having chiral phosphorus linkages are contemplated by the present invention. See Stec, W. J., and Lesnikowski, Z. J., in *Methods in Molecular Biology* Vol. 20: *Protocols for Oligonucleotides and Analogs,* S. Agrawal, Ed., Humana Press, Totowa, N.J. (1993), at Chapter 14. See also Stec, W. J. et al., *Nucleic Acids Research,* Vol. 19, No. 21, 5883–5888 (1991); and European Patent Application EP 0 506 242 Al, each of which are hereby incorporated by reference in their entirety.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

In preferred embodiments, compounds of the invention comprising the haloacetyl linker include those having the Formula V:

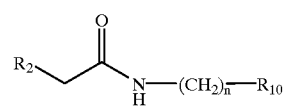

wherein:

$R_2$ is halogen which is preferably chlorine, or $R_2$ is a pendant group;

$R_{10}$ is a nucleobase, a nucleoside, a nucleotide, an activated nucleotide, an oligonucleotide, an oligonucleotide connected to a solid support, or a moiety of Formula VI:

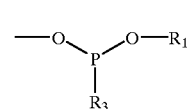

wherein:

$R_1$ is H or a phosphorus protecting group;

$R_3$ is $—N(R_4)_2$, or a heterocycloalkyl or heterocycloalkenyl ring containing from 4 to 7 atoms, and having up to 3 heteroatoms selected from nitrogen, sulfur, and oxygen;

$R_4$ is straight or branched chain alkyl having from 1 to 10 carbons; and n is from 1 to about 10.

In more preferred embodiments, compounds of the invention having the Formula VII:

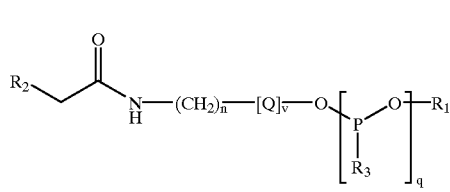

wherein:

v and q are each 0 or 1, provided that the sum of v and q is not 0;

q is 0 or 1;

Q has one of the Formulas II or III:

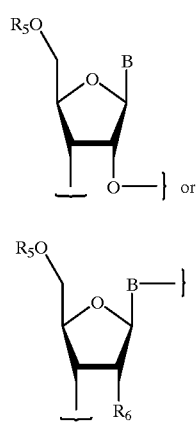

wherein:

$R_5$ is a hydroxyl protecting group;

B is a nucleobase;

$R_6$ is F, O—$R_{20}$, S—$R_{20}$ or N—$R_{20}(R_{21})$;

$R_{20}$ is alkyl, or a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic or heterocyclic;

and wherein any available hydrogen atom of said ring system is each replaceable with an alkoxy, alkylamino, urea or alkylurea group;

or $R_{20}$ has one of the formulas:

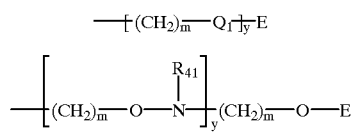

wherein $Q_1$ is O, S or $NR_2$;

m is from 1 to 10;

y is from 0 to 10;

E is N $(R_{21})(R_{31})$, N=C$(R_{21})(R_{31})$, $C_1$–$C_{10}$ alkyl, or $C_1$–$C_{10}$ substituted alkyl wherein said substituent is N $(R_2)(R_3)$;

each $R_{21}$ and $R_{31}$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from N and O; and $R_{41}$ is H or $C_1$–$C_{12}$ alkyl.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Example 1

(N-Chloroacetyl)-6-aminohexanol (1)

A solution of N,N'-dicyclohexylcarbodiimide (8.24 g, 40 mmol) in THF (50 mL) was added dropwise to a mixture of chloroacetic acid (3.78 g, 40 mmol) and N-hydroxysuccinimide (6.33 g, 55 mmol) in THF (30 mL) under magnetic stirring at 0–4° C. The stirring was maintained for 3 hours in an ice bath and for 4 hours at room temperature. The precipitate was filtered off, washed on the filter with THF (2×25 mL). The combined filtrates were evaporated in vacuo to one third of the initial volume (ca. 30 mL) and placed in an ice bath. A solution of 6-aminohexanol (4.69 g, 40 mmol) in THF (50 mL) was added dropwise under magnetic stirring. The reaction mixture was kept for 4 hours in an ice bath, and stirring was continued overnight at room temperature. The solution was evaporated in vacuo, and the residue was dissolved in water (50 mL) and filtered. The pH of filtrates was adjusted to 7.5–8 by adding 5% aq $NaHCO_3$, and the product was extracted with $CH_2Cl_2$ (5×30 mL). Combined extracts were dried over $Na_2SO_4$ and evaporated to a solid, which was re-crystallized from toluene to give (N-chloroacetyl)-6-aminohexanol (5.11 g, 66%) as white crystals, mp 65.5–66° C. $^1$H NMR (CDCl$_3$):δ 6.6 (1H, br. s) 4.05 (2H, s, ClCH$_2$); 3.65 (2H, t, J=6.2 Hz, OCH$_2$); 3.32 (2H, dt, J 6.3 Hz, NCH$_2$); 1.6–1.2 (9H, m, 4 CH$_2$ and NH). $^{13}$C NMR (CDCl$_3$): 165.85 (C=O); 62.65 (ClCH$_2$); 42.66 (OCH$_2$); 39.80 (NCH$_2$); 32.55, 29.31, 26.51, 25.34 (4'CH$_2$).

Example 2

2-Cyanoethyl (N-chloroacetyl)-6-aminohexyl (N,N-diisopropyl)phosphoramidite (2)

A solution of 1H-tetrazole (0.45 M in MeCN; 6.67 mL, 3.0 mmol) was added to a mixture of N-chloroacetyl-6-aminohexanol and 2-cyanoethyl N,N,N',N'-tetraisopropylphosphorodiamidite (1130 mg, 3.75 mmol). The mixture was magnetically stirred at room temperature for 1 hour, and the reaction was found completed by $^{31}$P NMR. The mixture was cooled to −10° C. and treated first with dry Et$_3$N (304 mg, 3.0 mmol; 25% in MeCN) and then with aqueous NaHCO$_3$ (5%; 10 mL) and saturated NaCl (20 mL). The product was extracted with toluene (3×40 mL) and dried over Na$_2$SO$_4$. The solvent was evaporated, the residue was dissolved in toluene (2 mL) and precipitated to hexane at −40° C. Liquid precipitate was dried on an oil pump to give 591 mg (50%) of 2-cyanoethyl (N-chloroacetyl)-6-aminohexyl (N,N-diisopropyl)phosphoramidite as colorless oil, $^{31}$P NMR (CD$_3$CN): 148.41.

Example 3

Oligonucleotide synthesis.

Oligonucleotide synthesis was performed on an ABI 380B DNA Synthesizer using phosphoramidite chemistry, standard ancillary reagents, cycles, and procedures. For preparation of phosphorothioate oligonucleotides, 3H-1,2-benzodithiol-3-one 1,1-dioxide (0.05 M in MeCN) was employed as the sulfur-transfer reagent. Phosphoramidite 1 (0.2 M in MeCN) was attached at the 5'-terminus on the last coupling step. Both capping subroutine and detritylation are neither required nor recommended as part of the last synthetic cycle. The solid support bound oligonucleotide was briefly dried on an oil pump and subjected to the attachment of a pendant group.

Example 4
Attachment of pendant groups
Treatment with Amines

Solid support bound oligonucleotides were treated with amines as shown under the conditions specified in the Table 1, below. The reaction mixture was diluted with conc. ammonia and left at room temperature for 2 hours. The solution was collected and evaporated to dryness. The residue was dissolved in water (2 mL) and treated depending on the reagent employed for the derivatization. For 5b,7b, and 8b solutions were neutralized with Dowex 50w×8 (PyH+), filtered, and analyzed by HPLC. For 6b, the emulsion was extracted with $CH_2Cl_2$ (5×0.5 mL), filtered, and analyzed by HPLC. For 3a,4a, and 4b no special treatment was required. The solutions were filtered and subjected to HPLC.

Treatment with Mercaptans

Solid support bound oligonucleotides were treated with mercaptans as shown under the conditions specified in the Table 1. The solid support was washed with dioxane (5×1 mL), concentrated aqueous ammonia was added, and the mixture was left for 2 hours at room temperature. The solution was collected and evaporated to dryness. The residue was dissolved in water (2 mL), filtered and analyzed by HPLC.

HPLC Techniques

Crude oligonucleotides were analyzed on a DeltaPak 15 m C18 300 HPLC column (3.8×300 mm) eluted with linear gradients a) for 3a, 4a, and 10a from 0 to 60% B in 40 minutes (0.1 M $NH_4OAc$ as buffer A; 0.1 M $NH_4OAc$ in 50% aq MeCN as buffer B); b) for 4b, 5b, 7b–10b from 0 to 25% B in 50 minutes; (0.1 M $NH_4OAc$ as buffer A; 80% aq MeCN as buffer B) c) for 6b, 11b, 12b from 0 to 100% B in 50 min, (0.1 M $NH_4OAc$ as buffer A; 80% aq MeCN as buffer B). Retention times for the oligonucleotides 3–12 are presented in the Table 1.

TABLE 1

Preparation of Tethered Oligonucleotides by Postsynthetis Conversion of Chloroacetyl Linker

| Oligo-nucleotide | | Reagents/ Conditions | Time, (hours) | Yield % | ES MS, MW Found | ES MS, MW Calculated | Retention time, min |
|---|---|---|---|---|---|---|---|
| 3a | | Conc. $NH_3/H_2O$ | 2 | 85 | 1999.3 | 1999.39 | 22.1[a] |
| 4a | | 1M n-$BuNH_2/H_2O$ | 6 | 90 | 2055.4 | 2055.54 | 23.7[a] |
| 4b | | 1M n-$BuNH_2$/EtOH | 12 | 84 | 3880.1 | 3880.68 | 35.7[b] |
| 5b | | 0.5M (n-Bu)$_2$NH/ EtOH | 12 | 34 | 3936.0 | 3936.76 | 43.5[b] |
| 6b | 10 | 0.25M n-$C_{12}H_{25}NH_2$/ dioxane °C. | 12 | 65 | 3992.2 | 3992.85 | 26.9[c] |
| 7b | | 0.5M Spermine/ DMF | 12 | 65 | 4010.1 | 4009.84 | 35.6[b] |
| 8b | | 0.5M L-lysine/ 0.25M DBU/50% aq DMF/55° C. | 12 | 35 | 3954.4 | 3953.7 | 32.3[b] |
| 9b | | 0.1M benzylmercaptane/ 0.5M $Et_3N$/ dioxane | 6 | 76 | 3917.9 | 3917.69 | 42.9[b] |
| 10a | | 0.1M p-thiocresol /0.2M $Et_3N$/ dioxane | 6 | 94 | 2106.3 | 2106.58 | 28.9[a] |
| 10b | 15 | 0.1M p-thiocresol /0.5M $Et_3N$/ dioxane | 6 | 86 | 3931.8 | 3931.72 | 42.8[b] |
| 11b | | 0.125M n-$C_{18}H_{37}SH$/ 0.125M DBU/ dioxane/55° C. | 12 | 62 | 4094.5 | 4094.01 | 37.5[c] |
| 12b | | 0.5M thiocholesterol/ 0.25M DBU/ dioxane/55° C. | 12 | 74 | 4210.3 | 4210.24 | 39.2[c] | a. 0 to 60% B in 40 min; A=0.1 M $NH_4OAc$; B=0.1 M $NH_4OAc$ in 50% aq MeCN.
b. 0 to 25% B in 50 min; A=0.1 M $NH_4OAc$; B=80% aq MeCN.
c. 0 to 100% B in 50 min; A=0.1 M $NH_4OAc$; B=80% aq MeCN.

The specific sequences of "a" and "b" are not germane to the invention. For completeness, it is noted that "a" is a homothymidine eight-mer while "b" is a homothymidine twelve-mer.

Examples 5–8
Preparation of 2'-O-aminoethyl-5'-O-DMT-5-methyluridine (15)

In some preferred embodiments, compounds of Formula I wherein v is 1 and Q has the Formula II can be prepared by reacting a tri(2-oxyethylphthalimido)borate with a 2,2'-anhydronucleoside. This is shown for the synthesis of 2'-O-aminoethyl-5'-O-DMT-5-methyluridine (15) in Examples 5–8 below.

Example 5
Preparation of 2'-O-phthalimidoethyl-5-methyluridine (13)

N-(2-Hydroxyethyl)phthalimide (277 g, 1.45 mol) was slowly added to a solution of borane in tetrahydrofuran (1 M, 600 mL) with stirring. Hydrogen gas evolved as the solid dissolved. Once the rate of bubbling subsided, the solution was placed in a 2 L stainless steel bomb. 2,2'-anhydro-5- methyluridine (60 g, 0.25 mol) and sodium bicarbonate (120 mg) were added and the bomb was sealed. After 30 minutes, the bomb was vented for the last time and then placed in an oil bath and heated to 150° C. internal temperature for 24 hours. The bomb was cooled to room temperature and opened. TLC revealed all the starting material was gone. The crude solution was concentrated and the residue was columned on silica gel starting with straight ethyl acetate to remove the excess phthalimide reagent followed by ethyl acetate-methanol 95/5 to elute the product to give 22.2 g (20.6%) of ca 90% pure product.

Example 6

Preparation of 2'-O-phthalimidoethyl-5'-O-DMT-5-methyluridine (14)

2'-O-phthalimidoethyl-5-methyluridine (22.2 g, 0.053 mol) was coevaporated with pyridine (2×75 mL) and then dissolved in 100 mL of pyridine. Dimethoxytrityl chloride (27 g, 0.080 mol) was added in one portion with stirring. TLC after 1 hour indicated a complete reaction. Methanol (10 mL) was added to quench the reaction. The reaction was concentrated and the residue was partitioned between ethyl acetate and saturated sodium bicarbonate solution (150 mL each). The organic layer was concentrated and the residue was dissolved in a minimum amount of dichloromethane and applied on a silica gel column. The compound was eluted with ethyl acetate-hexanes-triethylamine (50:50:1 to 80:20:1) to give 26.1 g (82%) of pure product.

Example 7

Preparation of 2'-O-aminoethyl-5'-O-DMT-5-methyluridine 15

2'-O-phthalimidoethyl-5'-O-DMT-5-methyluridine (21.1 g, 0.29 mol) was dissolved in methanol (500 mL). Anhydrous hydrazine (4.9 mL, 0.15 mol) was added and the solution was heated to reflux. TLC after 3 hours indicated a complete reaction. The solution was concentrated and columned on silica gel using methanol and then methanol-ammonium hydroxide (98:2) to give 10.4 g of pure product as a white foam and 2 g of slightly contaminated product (total yield 12.4 g, 71%). $^1$H NMR (CDCl$_3$)δ 7.67 (S, 1H), 7.25–7.46 (m, 9H), 6.86 (d, 4H, J=8.9H$_z$), 6.06 (d, 1H, J=4.12H$_z$), 4.45 (t, 1H, J=5.06H$_z$), 4.17 (m, 1H), 4.1 (t, 1H, J=4.56H$_z$), 3.99 (m, 1H), 3.81 (S, 6H), 3.56–3.68 (m, 2H), 3.53 (d, 1H, J=1.96H$_z$), 3.45 (d, 1H, J=2.56 H$_z$), 2.98 (t, 2H, J=3.48H$_z$), 1.39 (S, 3H). $^{13}$C (CDCl$_3$) d 164.96, 158.42, 151.3, 144.23, 135.32, 129.92, 127.97, 127.77, 126.87, 113.06, 110.93, 87.06, 86.58, 83.42, 70.60, 69.08, 62.42, 54.98, 45.69, 40.49, 11.71 MS (API-ES$^-$) calculated for C$_{33}$H$_{37}$O$_8$N$_3$ 603; observed 602.2.

Example 8

2'-O-[N-Chloroacetyl-2-(aminoethyl)] 5'-dimethoxy trityl-5-methyl uridine (16)

To chloroacetic anhydride (2.35 mol) in 10 mL of CH$_2$Cl$_2$, diisopropyl ethylamine is added at 0° C., followed by 2'-O-(aminoethyl)-5'-DMT 5-methyluridine (2.35 mmol). The mixture is stirred for 1 hour 0° C. TLC indicated (CH$_2$Cl$_2$/CH$_3$OH 9:1) complete conversion of amine into the amite derivative. The mixture is then diluted with CH$_2$Cl$_2$ (50 mL) and washed successively with aqueous NaHCO$_3$ solution, saturated NaCl solution and dried over MgSO$_4$. Chromatography over silica and elution with CH$_2$Cl$_2$:EtOAc gave the desired nucleoside.

Example 9

2'-O-[N-Chloroacetyl-2-(aminoethyl)] 5'-dimethoxy trityl-5-methyl uridine [N-3'-O-N,N-diisopropylaminocyanoethyloxy] phosphoramidite (18)

5'-O-DMT-2'-O-(N-chloroacetyl-2-aminoethyl)-5-methyluridine (1 mmol) is dissolved in 15 mL of dry CH$_2$Cl$_2$ and to this solution 85 mg of diisopropylaminotetrazolium salt (0.5 mmol) followed by 420 μL of 2-cyanoethyl-N,N,N'N'-tetraisopropyl phosphoramidite is added slowly using a syringe under argon. The mixture is stirred at room temperature overnight and in the morning the TLC will indicate almost complete reaction. 40 μL of the phosphitylation reagent is added and stirred for an additional 2 hrs. TLC then indicates complete conversion of the starting material to the phosphoramidite (CH$_2$Cl$_2$:EtOAc 50:50). The reaction mixture is diluted with 50 mL CH$_2$Cl$_2$, washed with saturated NaHCO$_3$ solution followed by saturated NaCl solution. The organic layer is dried over MgSO$_4$ and evaporated to dryness. The crude foam is purified in silica gel and eluted with 50:50 ethylacetate:CH$_2$Cl$_2$.

Example 10

2'-O-[N-chloroacetyl-(6-aminohexyl)]-5'-O-dimethoxytrityl-5-methyl-uridine (19)

To 3.3 g (5 mmol) of 2'-O-(6-aminohexyl)-5'-O-dimethoxytrityl-5-methyl uridine (prepared according to the procedure of Manoharan, M; Tivel, K. L., Andrade, L. K., Cook, P. D. Tetrahedron Lett. 36, 3647,1995) in 20 mL of anhydrous CH$_2$Cl$_2$, 1 mL of diisopropylethyl amine is added, followed by 1.2 g (5.6 mmol) of chloroacetic anhydride at 00C. The reaction mixture is stirred at 0° C. for 2 hours and tested for completion of reaction by TLC (CH$_2$Cl$_2$:CH$_3$OH 9:1). The reaction is complete and the reaction mixture is applied to silica gel equilibrated with CH$_2$Cl$_2$:CH$_3$OH 9:1 and eluted with the same to yield the desired compound.

Example 11

5'-O-DMT-2'-O-[N-chloroacetyl-(6-aminohexyl)]-5-methyl uridine-3'-O-(N,N-diisopropylamino-2-cyanoethyloxy) phosphoramidite (20)

The nucleoside from the previous step (2 mmol) is dissolved in 30 mL of anhydrous CH$_2$Cl$_2$ and to this solution 170 mg of diisopropylamino tetrazolium salt (1 mmole) followed by N,N,N'N'-tetraisopropyl-β-cyanoethoxyphosphoramidite (990 μL, 2.6 mmols) under argon atmosphere. The reaction mixture is stirred for 16 hours. TLC analysis (50:50 CH$_2$Cl$_2$/ethylacetate) indicated completion of the reaction. The reaction mixture was then diluted with 100 mL of CH$_2$Cl$_2$, extracted with saturated NaHCO$_3$ solution, washed with saturated NaCl solution and dried over MgSO$_4$. Evaporation to dryness to give a white foam. This white foam was applied on the top of silica gel which is made with CH$_2$Cl$_2$ containing 0.1% pyridine. The amidite was loaded in CH$_2$Cl$_2$ and eluted with 40:60 CH$_3$COOEt/CH$_2$Cl$_2$ to give the of purified amidite.

Example 12

General procedure for oligonucleotide synthesis Conjugation with 18 and 20

Compound 18 (0.39 mmol) is dissolved in 3.9 mL of anhydrous acetonitrile and loaded onto an Expedite Nucleic Acid Synthesis system (Millipore 8909) to synthesize the oligonucleotides. The concentration of amidites is 0.1M. The coupling efficiencies are more than 95%. For the coupling of the amidite 18 coupling time is extended to 10 minutes, and this step is carried out twice. All other steps in the protocol are supplied by Millipore are used as such. The oligomers are conjugated to amines or thiols in the controlled pore glass (CPG) supports and deprotected under standard conditions using concentrated aqueous NH40H (30%) at 55° C. 5'-O-DMT-containing oligomers are then purified by reverse phase high performance liquid chromatography (C-4, Waters, 7.8×300 mm, A=50 mM triethylammonium acetate, pH-7, B=acetonitrile, 5–60% of B in 60 min., flow 1.5 mL/min.). Detritylation with aqueous 80% acetic acid and evaporation, followed by desalting in a Sephadex G-25 column give modified oligonucleotides. Oligonucleotides were analyzed by HPLC, CGE and mass spectrometry.

Compound 20 (192 mg, 0.2 mmol) is dissolved in 2 mL of anhydrous acetonitrile and loaded onto an Expedite Nucleic Acid Synthesis system (Millipore) to synthesize the oligonucleotides. The amidite concentration is 0.1M. The coupling efficiencies are more than 95%. For the coupling of the amidite 20 coupling time is extended to 10 min. and this step is carried out twice. All other steps in the protocol supplied by Millipore are used except the extended coupling time for 20. The oligomers are conjugated to desired amines or thiols in the controlled pore glass (CPG) supports and deprotected under standard conditions using concentrated aqueous $NH_4OH$ (30%) AT 55° C. 5'-O-DMT-containing oligomers are then purified by reverse phase high performance liquid chromatography as in the previous case.

Example 13

Preparation of 5'-Dimethoxytrityl-$N^2$-[3-(N-chloroacetylpropylamino)]-2'-deoxyguanosine-3'-O-[2-cyanoethyl-N,N-diisopropyl]phosphoramidite A. 3',5'-O-(Tetraisopropyldisiloxane-1,3-diyl)-$N_2$-(3-aminopropyl)-9-(2'-deoxy-β-D-erythro-pentafuranosyl) guanosine (21)

This compound is prepared according to the reported procedure of Manoharan et al., Tetrahedron Lett., 43, 7675 (1996) 1,3-Diaminopropane (2.96 g, 40 mmol) in 2-methoxyethanol (50 ml) was heated to 100° C. To this hot stirred solution is added the 2-chloro-nucleoside 2',5'-O-Tetraisopropyldisiloxane-1,3-diyl-2-chloro-9-(2'-deoxy-β-D-erythropentafuronyl)-inosine (5.29 g, 10 mmol) in 2-methoxyethanol (70 ml) dropwise during a 6 hour period at 100° C. The reaction mixture was stirred at 100° C. temperature for 12 hours and evaporated to dryness. The residue was dissolved in methanol (150 mL) and cooled to 0° C. The precipitated solid was filtered and dried. The dried material was recrystalized from ethanol to give crystalline material:

mp 250–253° C.; yield 4.7 g (83%); $^1$H NMR ($Me_2SO$-$d_6$)δ 1.00 (m, 28 H), 1.55 (t, 2 H, $CH_2$), 2.62 (m, 1 H, $C_2H$), 2.80 (m, 1 H, $C_2H$), 3.22–4.00 (m, 9 H, $2CH_2$, $NH_2$, $C_5.CH_2$, $C_4H$), 4.74 (m, 1 H, $C_3H$), 6.14 (t, 1 H, $J_1$, 2'=6.20 Hz, $C_1H$), 6.72 (bs, 1H, NH), 7.78 (s, 1 H, $C_8H$). Anal. Calcd for $C_{25}H_{46}N_6O_5Si_2$. C, 52.97; H, 8.18; N, 14.83. Found: C, 52.59; H, 8.04; N, 14.56.

B. 3',5'-O-(Tetraisopropyldisiloxane-1,3-diyl)-$N_2$-(3-Chloroacetamido-propyl)-9-(2'-deoxy-β-D-erythropentofuranosyl)guanosine (22)

To a well stirred solution of the substrate 21 (16.9 mmol) in dry pyridine is added Hunig base (5.05 g, 50 mmol) followed by chloroacetic anhydride (17 mmol) slowly at 0° C. After the addition, the reaction mixture is stirred at room temperature for 2 h. The reaction is evaporated to dryness and the residue is dissolved in $CH_2Cl_2$ (150 mL). The organic extract is washed with 5% $NaHCO_3$ solution (50 mL), water (50 mL) and brine (50 mL). The extract is dried over anhydrous $MgSO_4$ and the solvent is removed under reduced pressure. The residue is purified by flash chromatography over silica gel using $CH_2Cl_2 \rightarrow$ acetone as the eluent. The pure fractions are collected and evaporated to give the desired product.

C. 3',5'-O-(Tetraisopropyldisiloxane-1,3-diyl)-6-O-diphenylcarbamoyl-$N_2$-(3-chloroacetamidopropyl)-9-(2'-deoxy-β-D-exythro-pentofuranosyl)-guanosine 23

To a well dried solution of the substrate compound 22 (7.5 mmol) in dry pyridine (100 mL) and dry dimethylformamide (50 mL) is added N,N-diisopropylethylamine (2.58 g, 20 mmol) and cooled to 0° C. unde argon atmospphere. To this cold stirred solution is added diphenylcarbamoyl chloride (3.46 g, 15 mmol) at once. After the addition of DPCCl, the reaction mixture is stirred at room temperature for 4 hours and evaporated to dryness. The residue is dissolved in $CH_2Cl_2$ (150 mL) and washed with 5% $NaHCO_3$ solution (50 mL), water (50 mL) and brine (50 mL). The $CH_2Cl_2$ extract is dried over anhydrous $MgSO_4$ and evaporated to dryness. The residue is purified by flash chromatography over silica gel using $CH_2Cl_2 \rightarrow$ EtOAc as the eluent. The pure fractions are collected and evaporated to give the desired product:

D. 6-O-Diphenylcarbamoyl-$N_2$-(3-chloroacetamidopropyl)-9-(2'-deoxy-β-D-exythro-pentofuranosyl) guanosine 24

The nucleoside 23 (8.32 g, 10.0 mmol) is dissolved in dry pyridine (75 mL) and allowed to stir at room temperature. To this cold stirred solution is added 0.5M tetrabutylammonium fluoride (80 mL, 40 mmol, prepared in py:THF:$H_2O$; 5:4:1) at once. The reaction mixture is stirred at room temperature for 15 minutes, the pH is adjusted to 7 with $H^+$+resin. The reaction is filtered, washed with methanol (50 mL) and the filtrate evaporated to dryness. The residue is dissolved in $CH_2Cl_2$ (150 mL), washed wtih water (50 mL) and brine (50 mL). The organic extract is dried over anhydrous $MgSO_4$ and evaporated to dryness. The residue is purified by flash chromatography over silica gel using $CH_2Cl_2 \rightarrow$ MeOH as the eluent. The pure fractions having the pure product are collected and evaporated to give the desired product.

E. 5'-O-(4, 41-Dimethoxytrityl)-6-O-diphenylcarbamoyl-$N_2$-(3-chloro-acetamidopropyl)-9-(2'-deoxy-β-D-exythropentofuranosyl)guanosine 25

The nucleoside 24 (5.90 mmol) is dissolved in dry pyridine (30 mL) and evaporated to dryness. The dried compound is dissolved in dry pyridine (100 mL) and treated with triethylamine (1.01 g, 10 mmol) under argon atmosphere. To this stirred solution is added 4,4'-dimethoxytrityl chloride (2.59 g, 7.67 mmol) and the stirring is continued at room temperature for 6 hours. The reaction mixture is quenched with methanol (20 mL), stirred for 10 minutes and evaporated to dryness. The residue is dissolved in dichloromethane (150 mL), washed with 5% $NaHCO_3$ solution (40 mL), water (40 mL) and brine (50 mL). The organic extract is dried over anhydrous $MgSO_4$ and the solvent is removed under reduced pressure. The residue is purified by flash chromatography over silica gel using $CH_2Cl_2 \rightarrow$ acetone as the eluent. The main fractions are collected and evaporated to dryness to give the title compound.

F. 3'-O-[(N,N-diisopropylamino)(β-cyanoethoxy) phosphanyl]-5'-O-(4,4'-dimethoxytrityl)-6-O-diphenylcarbamoyl-$N_2$-(3-trifluoroacetamidopropyl)-9-(2'-deoxy-β-D-exythropentofuranosyl)guanosine 26

The nucleoside 25 (4.3 g, 4.70 mmol) is dissolved in dry pyridine (30 mL) and evaporated to dryness. This is repeated three times to remove last traces of water and dried over solid sodium hydroxide overnight. Then it is dissolved in dry dichloromethane (100 mL) and cooled to 0° C. under argon atmosphere. To this cold stirred solution is added N,N-diisopropylethylamine (1.29 g, 10 mmol) followed by (8-cyanoethoxy)chloro(N,N-diisopropylamino)phosphane (2.36 g, 10 mmol) dropwise over a period of 15 minutes. The reaction mixture is stirred at 0° C. for 1 hour and at room temperature for 2 hours. The reaction mixture is diluted with dichloromethane (100 mL), washed with 5% NaHCO$_3$ solution (50 mL), water (50 mL) and brine (50 mL). The organic extract is dried over anhydrous MgSO$_4$ and the solvent is removed under reduced pressure. The residue is purified by flash chromatography over silica gel using CH$_2$Cl$_2$—>EtOAc containing 1% triethylamine as the eluent. The main fractions are collected and evaporated to dryness. The residue are dissolved in dry dichloromethane (20 mL) and added dropwise into a stirred solution of hexane (1500 mL), during 90 min. After the addition, the stirring is continued for additional 1 h at room temperature under argon. The precipitated solid is filtered, washed with hexane and dried over solid NaOH under vacuum overnight to give of the titled compound as colorless powder.

Example 14

Oligonucleotides Having an N2-Chloroacetyl Tether Present in Purines

The phosphoramidite compound, 5'-Dimethoxytrityl-N$^2$-(N-N-chloroacetylpropylamino-2'-deoxyguonosine-3'-O-[2-cyanoethyl-N,N-diisopropyl]phosphoramidite, is utilized in the DNA synthesizer as a 0.2M solution in anhydrous CH$_3$CN.

Oligonucleotide synthesis is carried out in either an ABI 380B or an ABI 394 synthesizer employing the standard synthesis cycles with an extended coupling time of 10 minutes during coupling of the modified amidite into the oligonucleotide sequence. Coupling efficiency of greater than 90% is observed.

A. N$^2$-Amine Linking Group Containing Phosphodiester Oligonucleotides

The following oligonucleotides having phosphodiester inter-nucleotide linkages were synthesized:

Oligomer 1: 5' TG*G GAG CCA TAG CGA GGC 3' (ICAM-1; P=O) (SEQ ID No: 1)

Oligomer2: 5' TG*G GAG CCA TAG* CGA GGC 3' (ICAM-1; P=O) (SEQ ID No: 2)

wherein G * represents a nucleotide functionalized to incorporate a N2-(3-N-chloroacetyl-propylamine) functionality. Oligomers 1 and 2 are antisense compounds targeted against the human ICAM-1 (Inter Cellular Adhesion Molecule-1).

B. N$^2$-propylamine Linking Group Containing Phosphorothioate Oligonucleotide

The following oligonucleotide having phosphorothioate inter-nucleotide linkages were synthesized:

Oligomer3: 5' TsG*sGs GsAsGs CsCsAs TsAsGs CsGsAs GsGsC 3' (ICAM-1; P=S) (SEQ ID No: 3)

wherein G* represents a nucleotide functionalized to incorporate a N$^2$-(3-N-chloroacetylpropylamine) functionality and the subscript "s" represents a phosphorothioate inter-nucleotide backbone linkage. These oligonucleotides are synthesized as per the previous method except during the synthesis, for oxidation of the phosphite moieties, the Beaucage reagent (i.e., 3H-1,2-benzodithioate-3-one 1,1-dioxide, see, Iyer, R. P., et al., *J. Am. Chem. Soc.* 1990, 112, 1253) is used as a 0.24 M solution in anhydrous CH$_3$CN solvent. The oligonucleotides were synthesized in the "Trityl-On" mode and purified by reverse phase HPLC.

Example 15

Functionalization Of Oligonucleotides At the N2-Position

The chloroacetyl tether in N2-position is functionalized with amines and thiols as described for the aminohexanol tether.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the present invention, and that such changes and modifications may be made without departing from the spirit of the invention. It is, therefore, intended that the appended claims cover all such equivalent variations as fall within the true spirit and scope of the invention.

What is claimed is:

1. A method for the preparation of a conjugated oligonucleotide comprising:

providing a compound of Formula I:

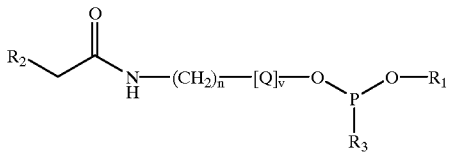

wherein:

$R_1$ is a phosphorus protecting group;

$R_2$ is selected from the groups consisting of chlorine and a pendant group;

$R_3$ is selected from the group consisting of —N(R$_4$)$_2$, a heterocycloalkyl ring containing from 4 to 7 atoms, a heterocycloalkenyl ring containing from 4 to 7 atoms, said heterocycloalkyl and heterocycloalkenyl rings each having up to 3 heteroatoms selected from nitrogen, sulfur, and oxygen;

$R_4$ is straight or branched chain alkyl having from 1 to 10 carbons.

v is 1 or 1;

n is 1 to about 10;

Q has one of the Formulas II or III:

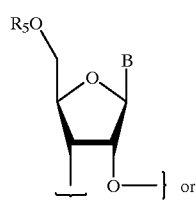   II or

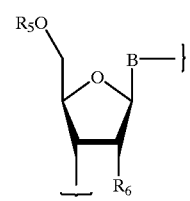   III wherein:

$R_5$ is a hydroxyl protecting group;

B is a nucleobase;

$R_6$ is selected from the group consisting of F, O—R$_{20}$, S—R$_{20}$ and N—R$_{20}$(R$_{21}$);

$R_{20}$ is alkyl, or a ring system having from about 4 to about 7 carbon atoms, or having from about 3 to about 6 carbon atoms and 1 or 2 hetero atoms, wherein said hetero atoms are selected from the group consisting of oxygen, nitrogen and sulfur and wherein said ring system is aliphatic, unsaturated aliphatic, aromatic and heterocyclic; and wherein any available hydrogen atom of said ring system is optionally replaced with an alkoxy, alkylamino, urea or alkylurea group;

or $R_{20}$ has one of the formulas:

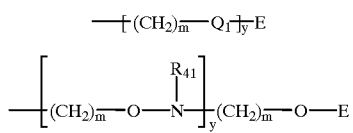

wherein $Q_1$ is O, S or NR$_2$;

m is from 1 to 10;

y is from 0 to 10;

E is N(R$_{21}$)(R$_{31}$), N=C(R$_{21}$)(R$_{31}$), C$_1$–C$_{10}$ alkyl, or C$_1$–C$_{10}$ substituted alkyl wherein said substituent is N(R$_2$)(R$_3$);

each $R_{21}$ and $R_{31}$ is, independently, H, C$_1$–C$_{10}$ alkyl, alkylthioalkyl, a nitrogen protecting group, or R$_2$ and R$_3$, together, are a nitrogen protecting group or wherein R$_2$ and R$_3$ are joined in a ring structure that can include at least one heteroatom selected from the group consisting of N and O; and $R_4$, is H or C$_1$–C$_{12}$ alkyl;

reacting said compound of Formula I with a compound of Formula IV:

IV

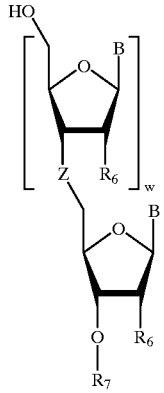

wherein:

R$_7$ is H, a hydroxyl protecting group, or a linker connected to a solid support;

w is 0 to about 100;

to form a compound of Formula IVa:

IVa

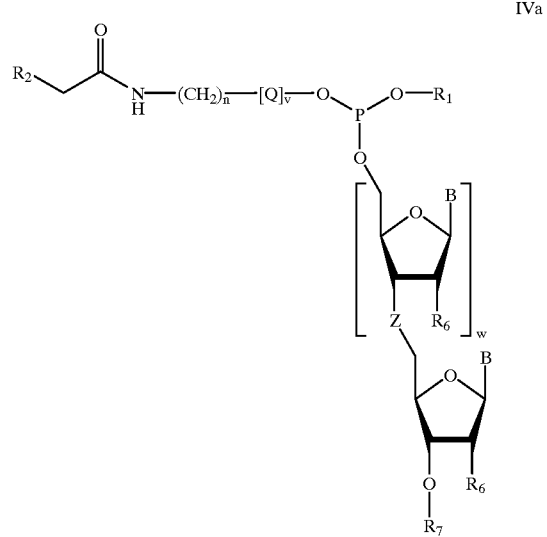

and contacting the compound of Formula IVa with a pendant group for a time and under conditions sufficient to form said conjugate.

2. The method of claim 1 further comprising oxidizing or sulfurizing said compound of Formula IVa to form a compound of Formula IVb:

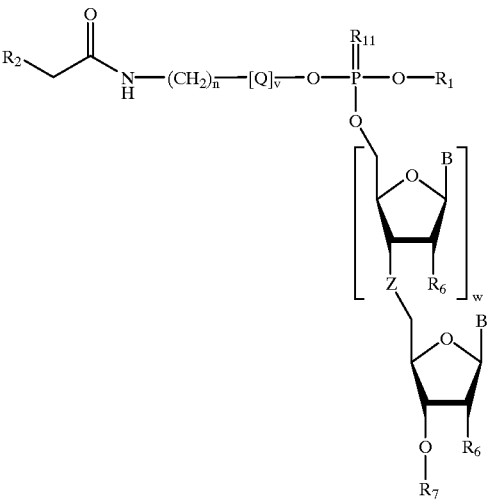

wherein R$_{11}$ is O or S.

3. The method of claim 1 wherein v is 0.
4. The method of claim 1 wherein v is 1.
5. The method of claim 1 wherein R$_2$ is Cl.
6. The method of claim 5 wherein R$_3$ is —N(R$_4$)$_2$, R$_4$ is isopropyl.
7. The method of claim 6 wherein R$_1$ is selected from the group consisting of β-cyanoethyl, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, and —CH$_2$CH$_2$N(CH$_3$)COCF$_3$.
8. The method of claim 6 wherein R$_1$ is β-cyanoethyl.
9. The method of claim 1 wherein n is 4 to 8.
10. The method of claim 1 wherein n is 6.
11. The method of claim 1 wherein R$_7$ is a linker connected to a solid support.
12. The method of claim 1 wherein said pendant group is an amine, a polyamine, a thiol, a protein, a peptide, or an amino acid.
13. The method of claim 3 wherein R$_2$ is Cl, R$_3$ is —N(R$_4$)$_2$, R$_4$ is isopropyl, R$_1$ is β-cyanoethyl, n is 6, R$_7$ is a linker connected to a solid support, and said pendant group is an amine, a polyamine, a thiol, a protein, a peptide, or an amino acid.
14. The method of claim 4 wherein R$_2$ is Cl, R$_3$ is —N(R$_4$)$_2$, R$_4$ is isopropyl, R$_1$ is β-cyanoethyl, n is 6, R$_7$ is a linker connected to a solid support, and said pendant group is an amine, a polyamine, a thiol, a protein, a peptide, or an amino acid, and Q has the Formula II.
15. The method of claim 4 wherein R$_2$ is Cl, R$_3$ is —N(R$_4$)$_2$, R$_4$ is isopropyl, R$_1$ is β-cyanoethyl, n is 6, R$_7$ is a linker connected to a solid support, and said pendant group is an amine, a polyamine, a thiol, a protein, a peptide, or an amino acid, and Q has the Formula III.
16. A method for the preparation of an activated phosphate compound of Formula:

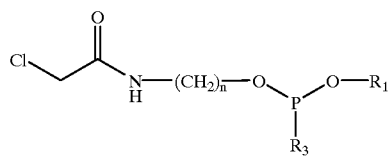

wherein:

R$_1$ is a phosphorus protecting group;

R$_3$ is —N(R$_4$)$_2$, or a heterocycloalkyl or heterocycloalkenyl ring containing from 4 to 7 atoms, and having up to 3 heteroatoms selected from nitrogen, sulfur, and oxygen;

R$_4$ is straight or branched chain alkyl having from 1 to 10 carbons; and n is 1 to about 10;

comprising:

providing a compound of Formula H$_2$N—(CH$_2$)$_n$—OH wherein n is 1 to about 10;

reacting said compound with a compound of Formula VIII:

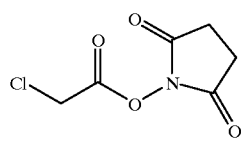

VIII to form a chloroacetylamino alkanol compound of Formula IX:

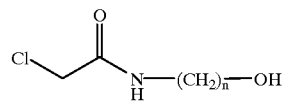

IX and contacting said chloroacetylamino alkanol compound with a reagent of Formula (R$_3$)$_2$P—O—R$_1$ for a time and under conditions sufficient to form said activated phosphite compound.

17. The method of claim 16 wherein R$_3$ is diisopropylamino; and R$_1$ is β-cyanoethyl.

18. The method of claim 16 further comprising reacting said activated phosphate compound with a free hydroxyl group of a nucleoside, a nucleotide, an oligonucleotide, or an oligonucleotide connected to a solid support to form a compound of Formula XI:

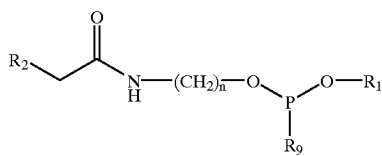

XI wherein R$_9$ is a nucleoside, a nucleotide, an oligonucleotide, or an oligonucleotide connected to a solid support.

19. The method of claim 18 further comprising oxidizing or sulfurizing said compound of Formula XI to form a compound of Formula XII:

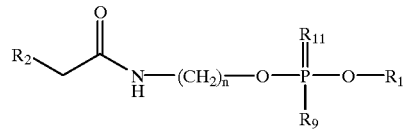

XII wherein R$_{11}$ is O or S.

20. The method of claim 19 further comprising coupling a pendant group to the compound of Formula XII.

21. The method of claim 20 wherein said pendant group is an amine, a polyamine, a thiol, a protein, a peptide, or an amino acid.

22. The method of claim 20 wherein said pendant group is an amine, a polyamine or a thiol.

23. A compound of Formula V:

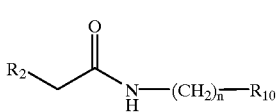

V wherein:

R$_2$ is halogen or a pendant group;

R$_{10}$ is a nucleobase, a nucleoside, a nucleotide, an activated nucleotide, an oligonucleotide, an oligonucleotide connected to a solid support, or a moiety of Formula VI:

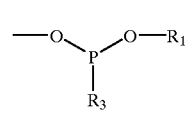

VI wherein:

R$_1$ is H or a phosphorus protecting group;

R$_3$ is —N(R$_{41}$)$_2$, or a heterocycloalkyl or heterocycloalkenyl ring containing from 4 to 7 atoms, and having up to 3 heteroatoms nitrogen, sulfur, and oxygen;

R$_4$ is straight or branched chain alkyl having from 1 to 10 carbons; and n is from 1 to about 10.

24. The compound of claim 23 wherein R$_{10}$ is a nucleoside, a nucleotide, an activated nucleotide, an oligonucleotide, or an oligonucleotide connected to a solid support.

25. The compound of claim 23 wherein R$_{10}$ has the Formula IV.

26. The compound of claim 23 having the Formula VII:

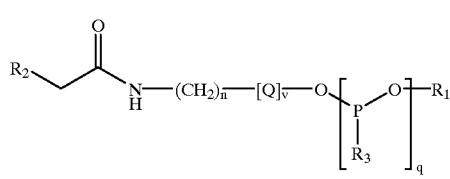

VII wherein:

v is 0 or 1;

q is 0 or 1;

Q has one of the Formulas II or III:

II

[Structure showing R5O-CH2 group attached to furanose ring with B (nucleobase) and O—} leaving position]

or

III

[Structure showing R5O-CH2 group attached to furanose ring with B—} and R6]

wherein:
$R_5$ is a hydroxyl protecting group;
B is a nucleobase;
$R_6$ is is F, O—$R_{20}$, S—$R_{20}$ or N—$R_{20}(R_{21})$;
$R_{20}$ is alkyl, or a ring system having from about 4 to about 7 carbon atoms or having from about 3 to about 6 carbon atoms and 1 or 2 hetero atoms wherein said hetero atoms are selected from the group consisting of oxygen, nitrogen and sulfur and wherein said ring system is aliphatic, unsaturated aliphatic, aromatic or heterocyclic;
and wherein any available hydrogen atom of said ring system is optionally replaced with an alkoxy, alkylamino, urea or alkylurea group;
or $R_{20}$ has one of the formulas:

—[(CH$_2$)$_{\overline{m}}$—Q$_1$]$_{\overline{y}}$E

—[(CH$_2$)$_{\overline{m}}$—O—N(R$_{41}$)]$_y$(CH$_2$)$_{\overline{m}}$—O—E wherein
$Q_1$ is O, S or $NR_2$;
m is from 1 to 10;
y is from 0 to 10;
E is $N(R_{21})(R_{31})$, $N=C(R_{21})(R_{31})$, $C_1$–$C_{10}$ alkyl, or $C_1$–$C_{10}$ substituted alkyl wherein said substituent is $N(R_2)(R_3)$;

each $R_{21}$ and $R_{31}$ is, independently, H, $C_1$–$C_{10}$ alkyl, alkylthioalkyl, a nitrogen protecting group, or $R_2$ and $R_3$, together, are a nitrogen protecting group or wherein $R_2$ and $R_3$ are joined in a ring structure that can include at least one heteroatom selected from the group consisting of N and O; and
$R_{41}$ is H or $C_1$–$C_{12}$ alkyl.

27. The compound of claim 26 wherein v is 0 and q is 1.
28. The compound of claim 26 wherein v is 1.
29. The compound of claim 26 wherein v is 1 and q is 1.
30. The compound of claim 26 wherein $R_2$ is Cl.
31. The compound of claim 30 wherein $R_3$ is —$N(R_4)_2$, wherein $R_4$ is isopropyl.
32. The compound of claim 31 wherein $R_1$ is selected from the soup consisting of β-cyanoethyl, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, and —CH$_2$CH$_2$N(CH$_3$)COCF$_3$.
33. The compound of claim 32 wherein $R_1$ is β-cyanoethyl.
34. The compound of claim 26 wherein n is 4 to 8.
35. The compound of claim 26 wherein n is 6.
36. The compound of claim 26 wherein v and q are each 1; and Q has the Formula III wherein the moiety —O—P(R$_3$)—O—R$_1$ is attached to B at the $N^2$ position.
37. The compound of claim 26 wherein v and q are each 1; and Q has the Formula II wherein the moiety —O—P(R$_3$)—O—R$_1$ is attached at the 2'-position.
38. The compound of claim 26 wherein said pendant group is an amine, a polyamine, a thiol, a protein, a peptide, or an amino acid.
39. The compound of claim 26 wherein v is 0; q is 1; $R_2$ is Cl, $R_3$ is —$N(R_4)_2$, $R_4$ is isopropyl, $R_1$ is β-cyanoethyl, n is 6, and said pendant group is an amine, a polyamine, a thiol, a protein, a peptide, or an amino acid.
40. The compound of claim 26 wherein v and q are each 1; $R_2$ is Cl, $R_3$ is —$N(R_4)_2$, $R_4$ is isopropyl, $R_1$ is β-cyanoethyl, n is 6, said pendant group is an amine, a polyamine, a thiol, a protein, a peptide, or an amino acid, and Q has the Formula II wherein the moiety —O—P(R$_3$)—O—R$_1$ is attached at the 2'-position.
41. The method of claim 26 wherein $R_2$ is Cl, $R_3$ is —$N(R_4)_2$, $R_4$ is isopropyl, $R_1$ is β-cyanoethyl, n is 6, said pendant group is an amine, a polyamine, a thiol, a protein, a peptide, or an amino acid, and Q has the Formula III wherein the moiety —O—P(R$_3$)—O—R$_1$ is attached at the $N^2$-position.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 1
tgggagccat agcgaggc                                                 18

<210> SEQ ID NO 2
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 2
tgggagccat agcgaggc                                                 18

```
<210> SEQ ID NO 3
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 3
tgggagccat agcgaggc                                                    18
```